(12) United States Patent  
Lee et al.

(10) Patent No.: US 8,349,004 B2  
(45) Date of Patent: Jan. 8, 2013

(54) SCLERAL BUCKLES FOR SUTURELESS RETINAL DETACHMENT SURGERY

(75) Inventors: Yau Wing Vincent Lee, Sha Tin (HK); Shun-Chui Dennis Lam, Kowloon (HK); Ta Li David Liu, Sha Tin (HK); Chi Lai Li, Sha Tin (HK)

(73) Assignee: The Chinese University of Hong Kong, Sha Tin, New Territories (HK)

( * ) Notice: Subject to any disclaimer, the term of this patent is extended or adjusted under 35 U.S.C. 154(b) by 205 days.

(21) Appl. No.: 12/471,759

(22) Filed: May 26, 2009

(65) Prior Publication Data

US 2010/0305694 A1    Dec. 2, 2010

(51) Int. Cl.
*A61F 2/14* (2006.01)
(52) U.S. Cl. ........................................ 623/4.1
(58) Field of Classification Search .................. 606/151, 606/157, 203, 204.25; 623/4.1, 6.63
See application file for complete search history.

(56) References Cited

U.S. PATENT DOCUMENTS

| | | | |
|---|---|---|---|
| 4,299,427 A | 11/1981 | Fauck | |
| 4,452,776 A | 6/1984 | Refojo | |
| 6,117,170 A | 9/2000 | Batdorf, Sr. | |
| 6,547,714 B1 | 4/2003 | Dailey | |
| 6,578,239 B2* | 6/2003 | Hatch | 24/16 PB |
| 2005/0177232 A1* | 8/2005 | Ashton | 623/6.63 |
| 2005/0203333 A1 | 9/2005 | Dailey et al. | |
| 2006/0167422 A1* | 7/2006 | Shahinpoor et al. | 604/294 |
| 2006/0271189 A1* | 11/2006 | Greenberg et al. | 623/6.63 |

FOREIGN PATENT DOCUMENTS

| | | |
|---|---|---|
| TW | 275387 B | 3/2007 |
| WO | WO 02/11648 A1 | 2/2002 |
| WO | WO 2007/065149 A3 | 6/2007 |

OTHER PUBLICATIONS

Custodis, "Treatment of retinal detachment by circumscribed diathermal coagulation and by scleral depression in the area of tear caused by imbedding of a plastic implant," Klin Monatsbl Augenheilkd 1956;129:476-495.
Lincoff et al., "Modifications to the Custodis Procedure for Retinal Detachment," Arch. Ophthalmol. 1965;73:160-163.
Schepens et al., "Scleral buckling procedures v. Synthetic sutures and silicone implants," Arch. Ophthalmol. 1960;64:868-881.
International Search Report and Written Opinion corresponding to the PCT application No. PCT/CN2010/072990, date of mailing Aug. 26, 2010, 14 pages total.

* cited by examiner

*Primary Examiner* — William H. Matthews
(74) *Attorney, Agent, or Firm* — Kilpatrick Townsend & Stockton LLP; Kenneth R. Allen; Ryan C. Sydenham (57) ABSTRACT

A set formed of a scleral buckle and an encircling band is provided for use in connection with retinal detachment surgery to enable the implantation of both the scleral buckle and encircling band free of any suture. A self-assembling scleral buckle-encircling band combination is secured in place by surface scleral tunnels operative as belt loops to enable the securing of a scleral buckle and encircling band on the eyeball to exert an intended indentation effect for treatment of retinal detachment.

19 Claims, 10 Drawing Sheets

SCLERAL BUCKLES FOR SUTURELESS RETINAL DETACHMENT SURGERY

CROSS-REFERENCES TO RELATED APPLICATIONS

NOT APPLICABLE

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

This invention relates to eye surgery and more particularly to aids for retinal detachment surgery.

The retina is a thin sheet of light sensitive nerve tissue lining the inner posterior of the eye and which functions to capture focused images like the film of a camera. Retinal detachment (RD) occurs when the retina separates from the posterior wall of the eye. It is usually caused by a break in the retina. Retinal detachment is one of the major human eye diseases which can lead to severe visual impairment or even blindness unless it is treated surgically.

Scleral buckling surgery is one of the most commonly performed surgical operations to treat retinal detachment. In the surgery as conventionally practiced, silicone rubber explants are sewed externally onto the scleral tissue (eye walls) overlying the retinal tear. The explants indent the sclera against the retina and close retinal tear by relieving the force tracking on the tear. These explants are known as scleral buckles. Scleral buckles are provided in a variety of sizes and shapes to treat different sizes of retinal breaks. Usually, a long silicone strip known as encircling band is also sutured and tightened onto the globe of the eye to further relieve forces pulling up the retina from the posterior wall. To complete the surgery, cryotherapy is applied externally to achieve a permanent adhesion between the retina and underlying tissue, to prevent the retina from re-detachment.

Commercially available buckle and encircling bands are still used according to a method based on an invention by Custodis in the early 1950s (Custodis E. "Treatment of retinal detachment by circumscribed diathermal coagulation and by scleral depression in the area of tear caused by imbedding of a plastic implant," Klin Monatsbl Augenheilkd 1956; 129: 476-495). The major differences from the original invention are the material used and the configurations of the buckles. The material used is either a silicone sponge which was pioneered by Lincoff et al. (Lincoff H A, Baras I, McLean J., "Modifications to the Custodis Procedure for Retinal Detachment," Arch. Ophthalmol. 1965; 73:160-163) or a solid silicone element which was pioneered by Schepens (Schepens C L, Okamura I D, Brockhurst R J, Regan C D, "Scleral buckling procedures v. Synthetic sutures and silicone implants," Arch. Ophthalmol. 1960; 64:868-881). The method of securing the scleral buckle and encircling band onto the scleral wall by suturing has remained virtually unchanged for more than 50 years.

Although scleral buckling surgery is effective, it is also a highly demanding surgical procedure with potential major complications. For example, the buckle and encircling band are conventionally sutured onto the sclera with a fine needle, and the suture depth is aimed at the half thickness of the very thin sclera (0.5-1 mm). If the placement of needle is too deep, the sclera will be accidentally perforated. Perforation of sclera may damage the underlying tissue, leading to bleeding or retinal hole formation, surgical failure and permanent damage. However, if the placement of the needle is too shallow, the buckle or encircling band could be loosened or even exposed out from the eye after the surgery. A loosened or exposed buckle also leads to surgical failure, infection and unwanted pain.

Apart from perforation of the globe, suturing poses at least one more disadvantage. For securing one suture, there are two bites: the anterior anchor and the posterior anchor. The anterior anchor site is relatively easy to reach. However, the posterior anchor is usually located posterior to the equator of the globe, and this location is relatively difficult to reach. The working space for making the posterior anchor is usually very limited because of the funnel shape of the bony orbit and the posterior location of the anchor site. Sometimes the surgeon must pull the extra-ocular muscle with a bridle suture in order to rotate the eye ball to yield more working space for applying the suture. The patient may experience great pain during this step and sometimes patient's heart rate may be decreased because of oculo-cardic reflex. Moreover, the posterior anchor can be located close to the exit of the vortex vein. If the vortex vein is accidentally perforated, profound bleeding can lead to failure of the whole surgery.

U.S. Pat. No. 4,299,227—Ophthalmologic appliance of Lincoff describes a method of treating retinal detachments through a small conjunctival incision wherein an expandable balloon like device is inserted into Tenon's space of the eye. The balloon is then expanded, to form a temporary indentation in the eye, and the balloon is deflated and removed from the eye after the retina has re-attached. There is no permanent indention effect onto the retina because the balloon is removed from the eye once the retina is re-attached in the early postoperatively period. The retinal detachment has higher chances of re-detaching when the indentation is removed, especially when there is proliferative vitreo-retinopathy during mid or late postoperative period.

U.S. Pat. No. 4,452,776—Hydrogel implant article and method of Refojo describes a hydrogel buckle of significant softness, pliability and elasticity when dry as well as when wet. It is sutured onto the scleral wall to produce the indentation effect. It claimed to be better than silicone in that it will swell up post-operatively to give a greater indentation effect. However, it can swell unexpectedly up to four fold of its original size years after the surgery because of hydrolytic degradation, thus potentially causing serious complications such as buckle extrusion, intrusion, squint and subcutaneous mass, etc. Production of this device was halted in mid 90's.

U.S. Pat. No. 6,547,714—Magnetized scleral buckle for use with silicone magnetic fluids in the treatment of retinal diseases, and U.S. Pat. No. 6,135,118—Treatment with magnetic fluids, both by Dailey describe a method to treat retinal detachment by the combined usage of a magnetic fluid tamponade inside the eye with a magnetized flexible scleral buckle placed outside the eye. The magnetic fluid is injected into the eye using a syringe, and the magnetic scleral buckle is positioned and immobilized in place, generally by suture or adhesive. The scleral buckle needs to be fixed in place by sutures or adhesives, which inevitably pose the same hazards as conventional scleral buckling surgery.

U.S. Patent Publication US2006/06167422 A1-Heat shrink scleral band with custom-made buckle for retinal detachment surgery of Mohsen Shahinpoor et al. discloses a scleral band of polymeric material that is capable of shrinking when it is stimulated by heat (hot-tip), laser, radio-frequency or other conventional means. In the Shahinpoor system, a progressively increasing indention effect is created by the progressive tightening of the scleral band. It is noted that the system requires a number of stages of follow-up procedures to produce the progressively increasing indention effect. The scleral band is inserted into the Tenon's space, but there is no mechanism described to stabilize the scleral band onto the eyeball. There is no external drainage of subretinal fluid. It aims at internal self-absorption of subretinal fluid. The ends of the scleral band are joined together by self-locking serrated ends. The scleral band can be combined with one snap-on custom-made buckle by an insertion peg to achieve scleral indention over the retinal tear region. The invention aims at merely a temporary indention (at least three days) and the whole implant is designed to be removed from the eye when the retina is re-attached.

If scleral buckling surgery can be improved, the risk is much reduced and the success rate is increased.

SUMMARY OF THE INVENTION

According to the invention, a combination of a scleral buckle and an encircling band is provided for use in connection with retinal detachment surgery to enable the implantation of both the scleral buckle and encircling band free of any suture. A self-assembling scleral buckle-encircling band combination is secured in place by surface scleral tunnels operative as belt loops to enable the securing of scleral buckle and encircling band on the eyeball to exert an intended indentation effect for treatment of retinal detachment.

The device and associated procedure reduce intraoperative risk of globe perforation during the procedure, thus reducing the chance of disastrous complications such bleeding, retinal hole formation and softening of the globe. In addition, the device simplifies the procedure, so the length of time of surgery is reduced and patient comfort is increased.

A device according to the invention could be easily combined with other options of retinal detachment treatment including pars plana vitrectomy, increasing surgical effects synergistically.

The buckle and encircling band according to the invention can be more securely implanted onto the globe. Therefore the postoperative risk of a loosened buckle can be reduced, enhancing the surgical success rate and minimizing the need for repeated surgery.

For a complete understanding of the present invention, reference is made to the following detailed description taken in conjunction with the accompanying drawing figures wherein like reference characters denote corresponding parts throughout the several views.

DETAILED DESCRIPTION SPECIFIC EMBODIMENTS

According to the invention, a combination of a scleral buckle and an encircling band are provided to enable the implantation of a scleral buckle and encircling band to repair retinal detachment without the need of suturing. Instead of performing multiple suturing, only four sets of surface incisions are made to produce scleral tunnels on the scleral wall for implantation of the sutureless scleral buckling system.

To this end, a set of sutureless scleral buckles and encircling band are provided for use in connection with retinal detachment surgery. These explants are particularly configured so as to allow anchoring on eye globe without suturing. An important feature is the ability of self assembly between the scleral buckle and encircling band, forming a united unit of a scleral buckle-encircling band complex, for implantation onto the globe as a unit. Four partial thickness scleral tunnels are created on the scleral wall for implantation of the scleral buckle-encircling band complex. The making of scleral tunnels is relatively easy compared with making sutures. First, the site of the scleral tunnel is usually made at the relatively accessible equator of the globe, where the sclera at equator is relatively thicker than that at the extraocular muscle insertion. Second, a crescent knife may be used to make the scleral tunnel, a knife that is wider than the conventional needle used in suturing, thus reducing the risk of globe perforation by the conventional spatula needle and cheese wiring used in a suture. Moreover, since the total area of anchor is increased, the buckle and the encircling band are less likely to be loosened postoperatively.

According to the invention, the scleral buckle is self assembled with the encircling band and hence it is secured onto the eyeball indirectly by locking with the encircling band. Three embodiments for the sutureless scleral buckling system are described herein. The embodiments differ in the manner of assembly between the scleral buckle and encircling band.

Embodiment I

Main Scleral Buckle

Figure 12:
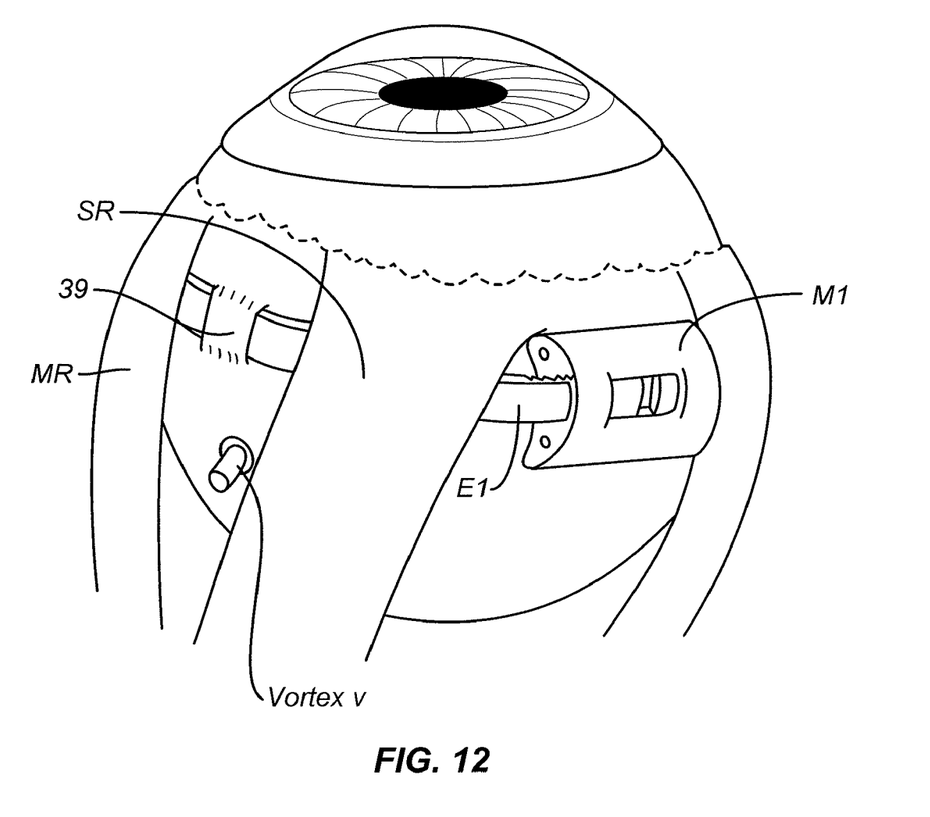
FIG. 12 is a perspective view of an eye illustrating circumferential scleral buckling without sutures.
Figure 13:
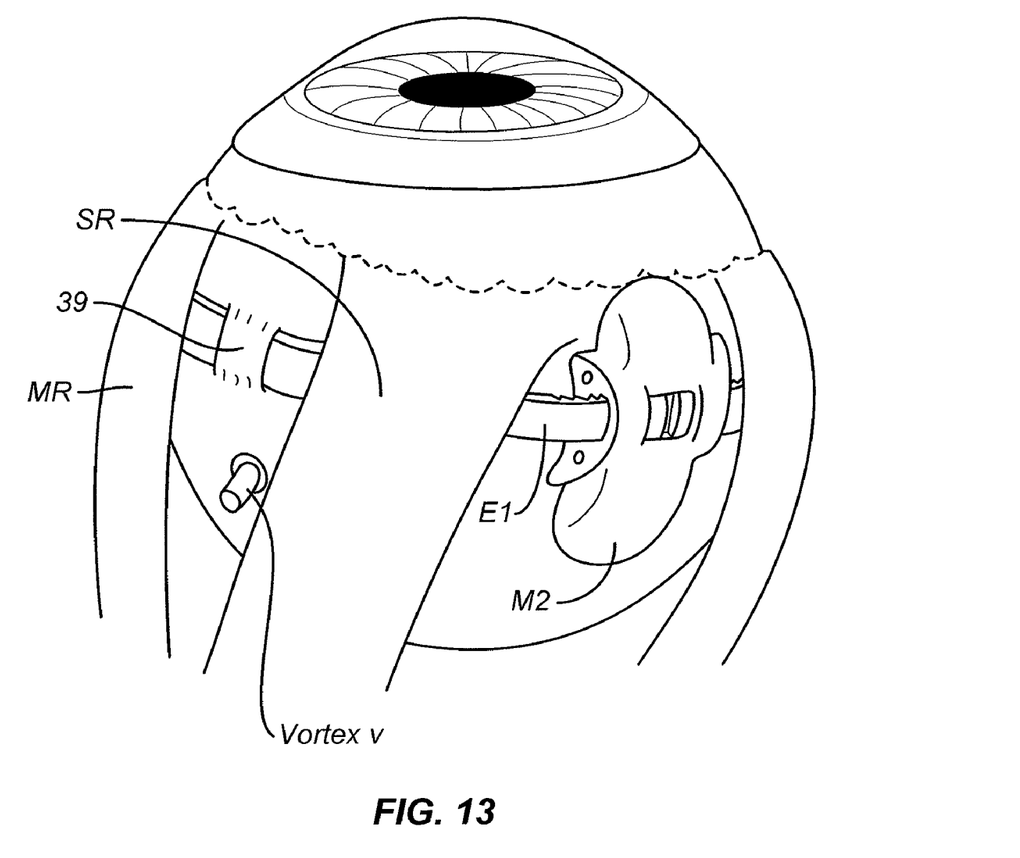
FIG. 13 is a perspective view of an eye illustrating radial scleral buckling without sutures.

FIG. 12 depicts a perspective view of a main circumferential scleral buckle in a first embodiment of the invention in use, and FIG. 13 depicts an additional perspective view of a main radial scleral buckle in the first embodiment in use. In the first embodiment, there are two types of scleral buckles: the main scleral buckle and the optional supplementary scleral buckle. All use an encircling band E1. All are made with medical grade silicone rubber. Other embodiments of the scleral buckles are mounted in a similar fashion and are therefore not shown as mounted.

Figure 1A:
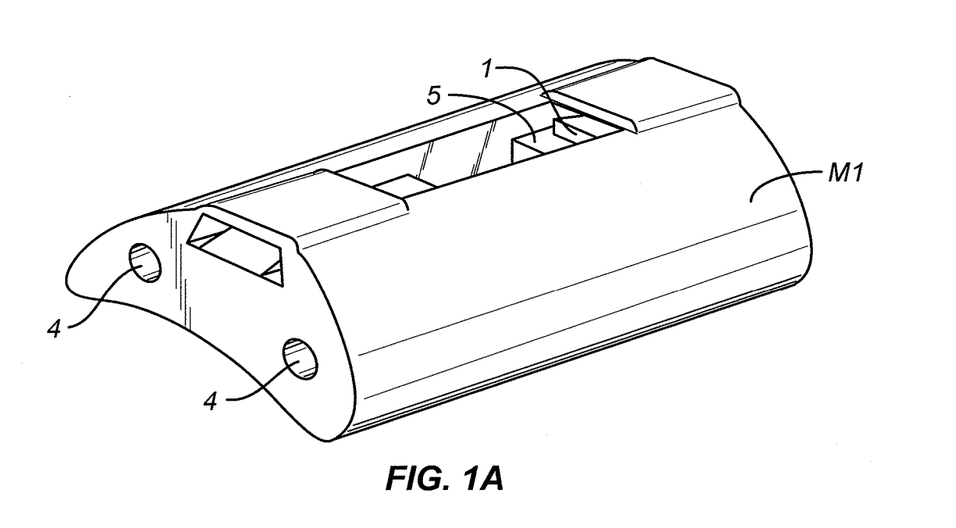
FIG. 1A is a perspective view of a main circumferential scleral buckle for implantation according to a first embodiment of the present invention.
Figure 1B:
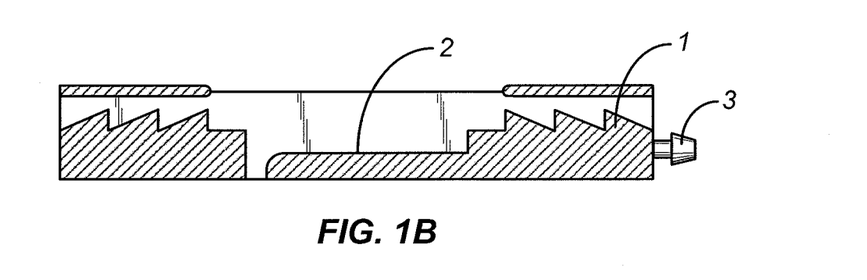
FIG. 1B is a side cross sectional view according to the first embodiment of the invention.
Figure 1C:
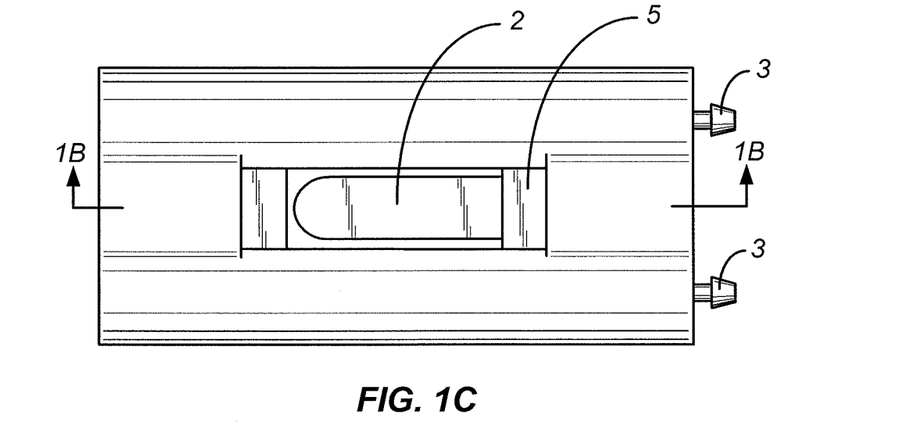
FIG. 1C is a top view according to the first embodiment of the invention.
Figure 2:
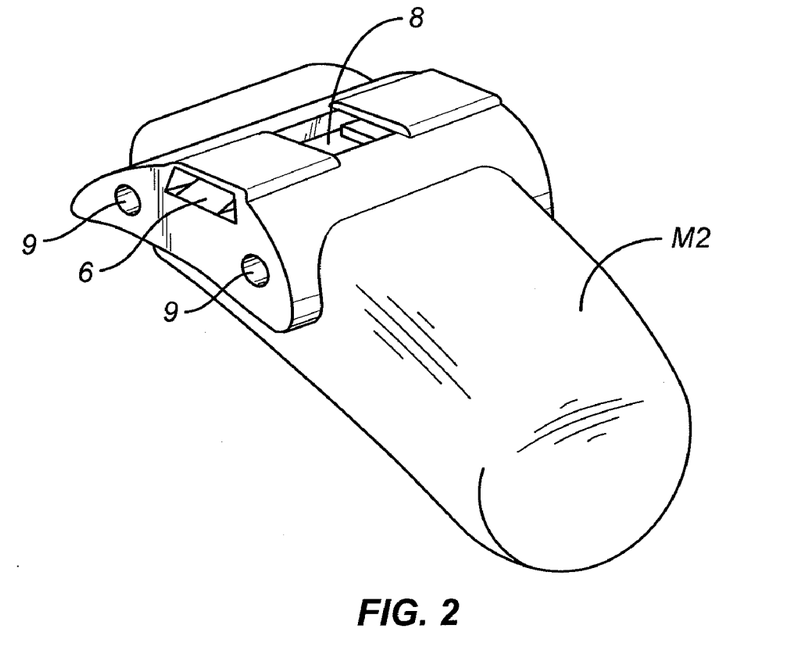
FIG. 2 is a perspective view of a main radial scleral buckle for implantation according to the first embodiment of the present invention.
Figure 3A:
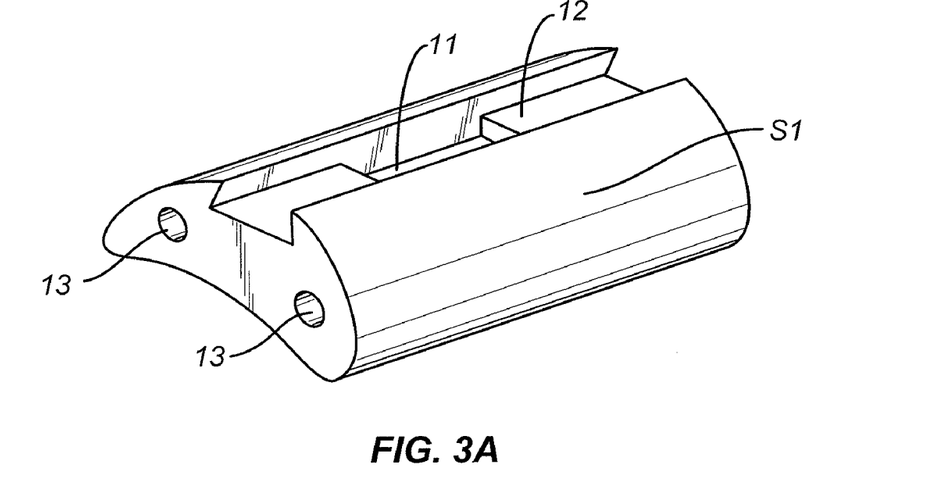
FIG. 3A is a perspective view of a supplementary circumferential scleral buckle for implantation according to the first embodiment of the present invention.
Figure 3B:
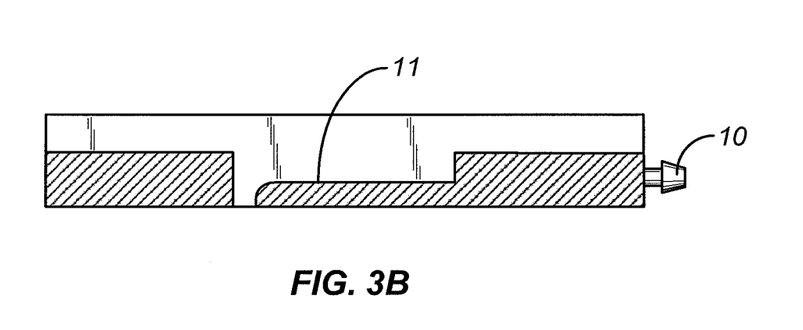
FIG. 3B is a side cross sectional view according to the first embodiment of the invention.
Figure 3C:
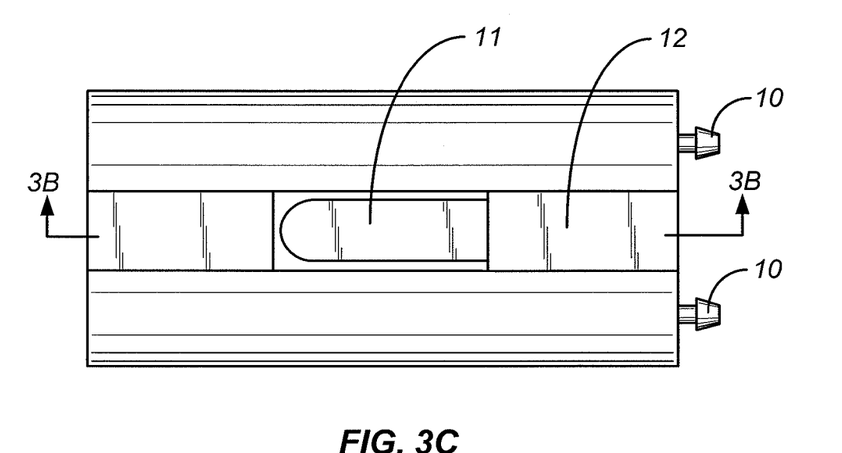
FIG. 3C is a top view according to the first embodiment of the invention.

The structure features a main or major scleral buckle and an optional supplementary scleral buckle and an encircling band. The main scleral buckle has two configurations, circumferential M1 (FIGS. 1A-1C and FIG. 12) and radial M2 (FIG. 2 and FIG. 13). The main scleral buckle M1 or M2 directly locks and tightens the two ends of the encircling band E1 (FIGS. 12, 13) with locks 1, 6 and forms the most important indentation effect onto the eyeball directly over the site where there is a retinal break inside the eyeball. The two locks on the main scleral buckle of the first embodiment have asymmetric castellations with a sawtooth profile that serves to lock with the complementary castellations with a sawtooth profile 17 at both ends of the encircling band E1. There is a lateral snap fit joint 3, 4, 7 (not shown), 9 to allow assembling with a supplementary scleral buckle S1 (FIGS. 3A-3C) or S2 (FIG. 4) having mating snap fit joints 10, 13, 14 (not shown), 16. A main buckle M1 or M2 is used in all cases.

Supplementary Scleral Buckle

Figure 4:
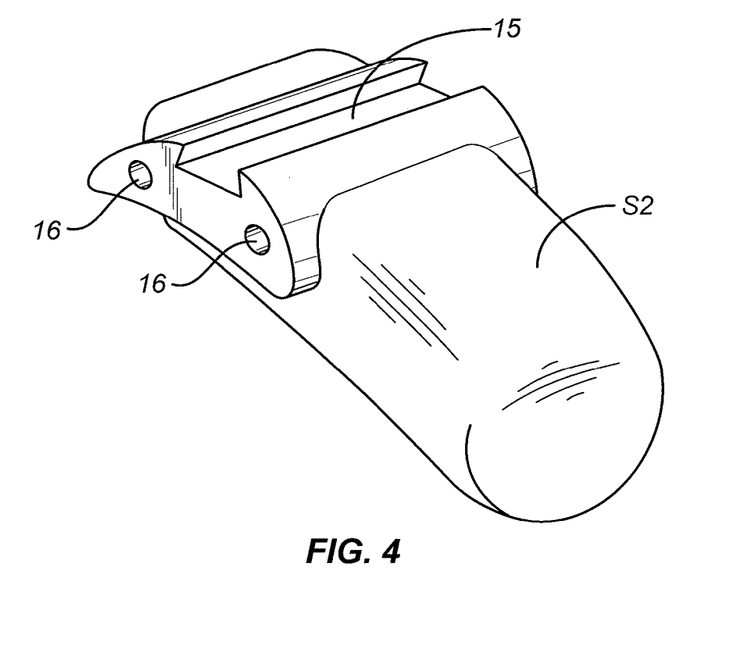
FIG. 4 is a perspective view of a supplementary radial scleral buckle for implantation according to the first embodiment of the present invention.

The supplementary scleral buckle has two configurations: circumferential S1 (FIGS. 3A-3C) and radial S2 (FIG. 4). These optional buckles are to be assembled with the encircling band E1 away from or side by side to the major scleral buckle M1 or M2. A supplementary buckle is medically indicated in the occasional cases where the lesion is wider than the length of the major buckle or where there are multiple retinal lesions located in more than one quadrant of the retina. There are lateral snap fit joints 10, 13, 14 (not shown), 16 on both front and back sides to allow stacked assembly by attachment to the main scleral buckle or additional supplementary scleral buckles. The common feature of the main and supplementary scleral buckles is the snap fit groove 5, 8, 12, 15, 105 on the external surface of the scleral buckle to accommodate the encircling band E1.

The Encircling Band

Figure 5:
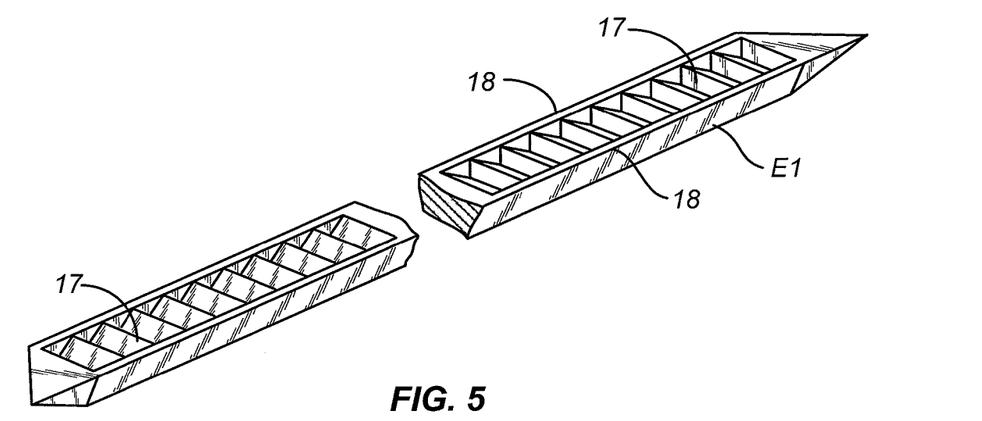
FIG. 5 is a perspective view of an encircling band according to the first embodiment of the present invention showing the interior of the band.

The encircling band E1 has one fixed size (typically 2.5 mm wide by 0.8 mm high and 120 mm long) with a typical 25 mm length of sawtooth profiles 21 at each end of the encircling band as shown in FIG. 5 for use to lock with the main scleral buckles M1, M2. The encircling band E1 can also assemble with supplementary buckles S1, S2. The encircling band itself is affixed to the globe by passing through four scleral tunnels 39 made on the scleral wall at or near the level of the globe equator, which resemble belt loops. After the band is passed through the scleral tunnels 39, the two ends of the encircling band are inserted into the locks 1, 6 at each side of the main scleral buckle M1, M2. The castellations with a sawtooth profile 17 on both ends of the encircling band E1 are complementary to the castellations with a sawtooth profile of the two locks 1, 6 on the main scleral buckle M1, M2 to lock both of them together. The two ends of the encircling band E1 are pulled towards each other until both the buckle and encircling band have exerted appropriate indentation effect on the eyeball and they lock against the vertical walls of the castellations. Redundant ends of the encircling band are trimmed off. Moreover, there is a step element 18 on either side and along the whole length of the band for snap fit into the groove 5, 8, 12, 15 of all types of buckles (main or supplementary). Thus, this is the method for assembling between a supplementary buckle and an encircling band.

In the above mentioned embodiment, the whole set comprising scleral buckles and encircling band can be secured onto the eyeball and exert appropriate indentation effect onto the eyeball without any need of sutures.

Choosing Type and Combination of Buckle

There are two types of major scleral buckles M1, M2 and supplementary scleral buckles S1, S2 respectively to treat different shapes and distributions of the retinal lesions which cause retinal detachment. The different combinations of scleral buckles and encircling band can be tailored to treat an individual's retinal detachment, and the assembly of scleral buckle with the encircling band E1 is simple. To be more specific, the circumferential scleral buckle M1 is chosen in case of retinal breaks orientated in a circumferential manner such as lattice degeneration or rows of retinal holes/tears. The radial scleral buckle M2 is chosen in case of retinal breaks orientated in a radial manner such as horse shoe tear. When there are retinal breaks located primarily in one quadrant on the retina, only the main scleral buckle M1 or M2 plus the encircling band E1 are needed. When there are retinal breaks located in more than one quadrant on the retina, a combination of a supplementary scleral buckle of either or both S1 and/or S2 plus the main scleral buckle M1 or M2 and the encircling band E1 is used.

When to Use the Tongue of the Scleral Buckle

In some embodiments of buckle, a central tongue structure 2, 11 is provided at the base of the groove 5, 12 in the scleral buckle. In the process of scleral tunnel-making, the 4 scleral tunnels 39 are made in-between the scleral muscle, since the scleral tunnel cannot be made underneath the rectus muscle of the eyeball. When the retinal break is located in between the rectus muscle, the scleral buckle should be also implanted in between the rectus muscle, right on top of the location of the retinal breaks. In this circumstance, the tongue 2 of the main scleral buckle is useful: The tongue is inserted through the scleral tunnel 39 in the quadrant of the retinal break, and the encircling band E1 needs to pass through the rest of the 3 scleral tunnels only. Antero-posterior movement of the main scleral buckle M1 is prevented by the union between the tongue 2 and the scleral tunnel 39.

When the retinal break is located underneath the rectus muscle, the scleral buckle should be implanted underneath the rectus muscle. In this circumstance, the tongue 2 of the main scleral buckle is not used. The encircling band E1 will pass through all the 4 scleral tunnels 39 only. Antero-posterior movement of the main scleral buckle is prevented by rectus muscle insertion and the two scleral tunnels for the encircling band close to the ends of the buckle.

Assembly of the Scleral Buckles and the Encircling Band.

Three different types of locking systems are used for fixation between the scleral buckles and encircling band.

1. Lock between the main scleral buckle and the encircling band—the interlocking joint 1, 6 with sawtooth profile 17.

2. Lock between the main scleral buckle with the supplementary buckle—3, 4, (7 not shown), 9, 10, 13, (14 not shown), 16 the snap-fit joint (frictional form-fitting joint).

3. Encircling band with a supplementary buckle—the snap-fit joint 12, 15, 18 (frictional joint).

Embodiment II

Figure 6A:
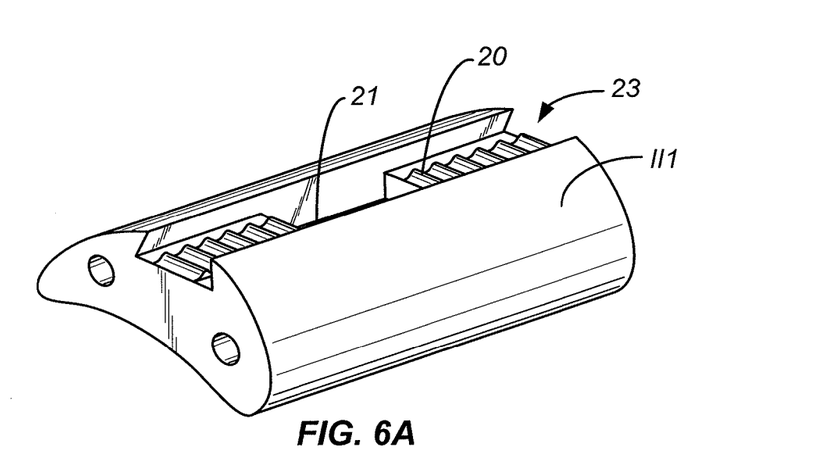
FIG. 6A is a perspective view of a circumferential scleral buckle for according to a second embodiment of the present invention.
Figure 6B:
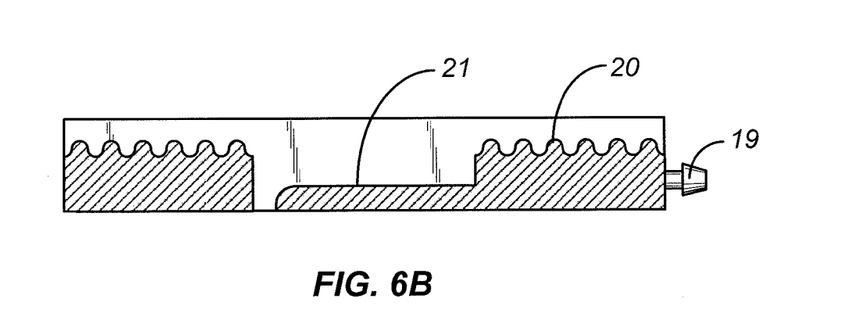
FIG. 6B is a side cross sectional view according to the second embodiment of the invention.
Figure 6C:
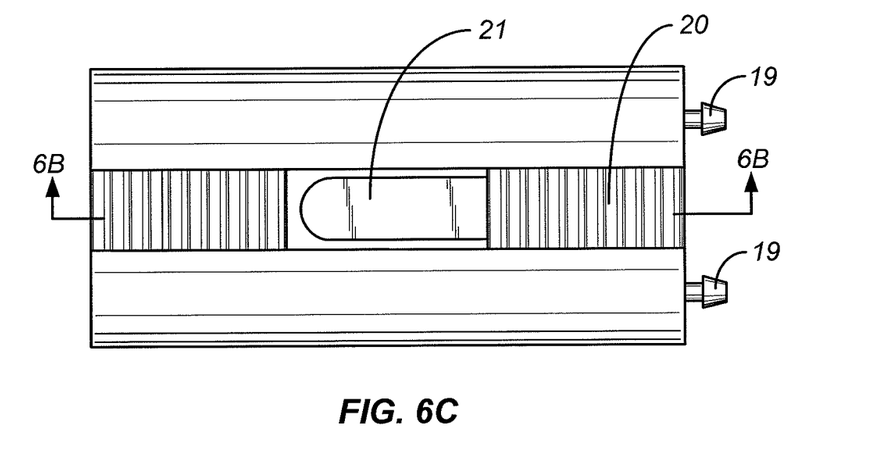
FIG. 6C is a top view according to the second embodiment of the invention.

In a second embodiment, there is only one type of scleral buckle (with 2 configurations: radial (FIG. 6A-6C) and circumferential (FIG. 7) to assemble with an encircling band E2. The basic principle, material and rationale for choice of configuration of scleral buckle are the same as that of embodiment I. The difference between embodiment I & II lies in the method of locking between the scleral buckle and encircling band. In this embodiment, both ends of the encircling band are locked together directly by a silicone sleeve (not shown) after the encircling band E2 has passed through the four scleral tunnels. The scleral buckle does not function as the main lock to hold and tighten the two ends of the encircling band. The buckle is assembled with the encircling band to exert indentation effect onto the eyeball. (FIG. 8).

The Scleral Buckle

Figure 7:
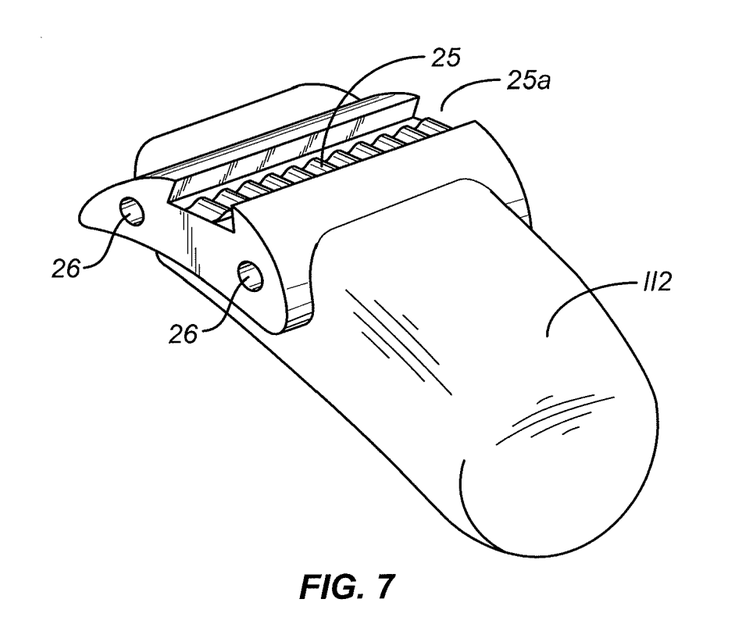
FIG. 7 is a perspective view of a radial scleral buckle for implantation according to the second embodiment of the present invention.
Figure 8A:
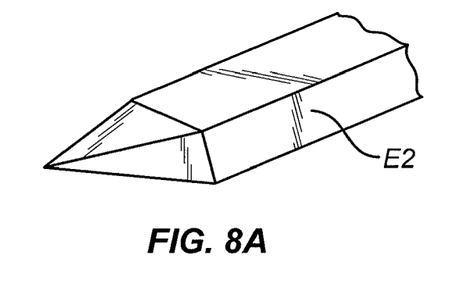
FIG. 8A is a perspective view of an encircling band according to the second embodiment of the present invention showing the exterior of the band.
Figure 8B:
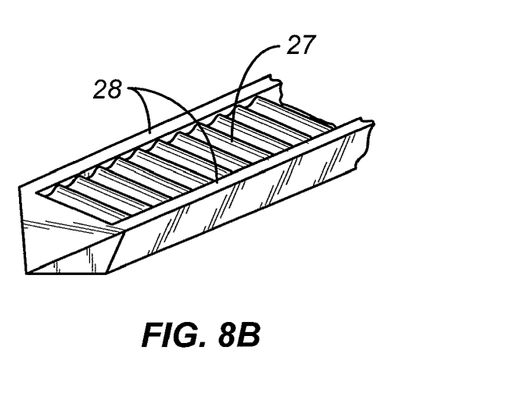
FIG. 8B is a perspective view of an encircling band according to the second embodiment of the present invention showing the interior of the band.
Figure 9A:
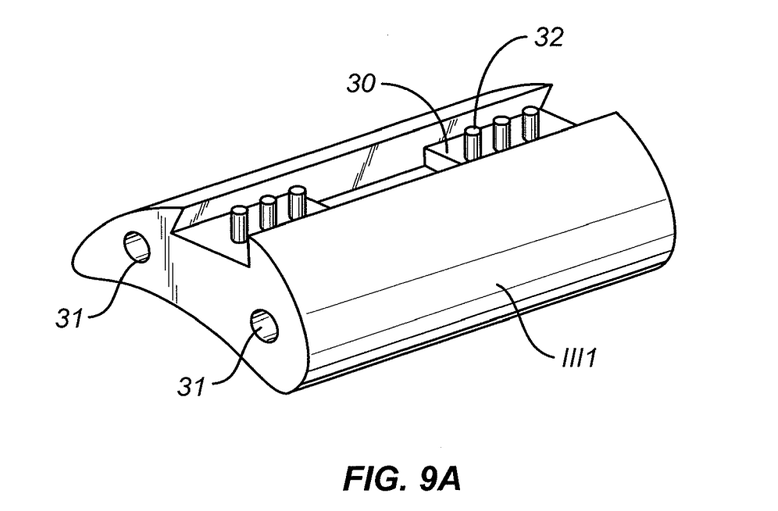
FIG. 9A is a perspective view of a circumferential scleral buckle for implantation according to a third embodiment of the present invention.
Figure 9B:
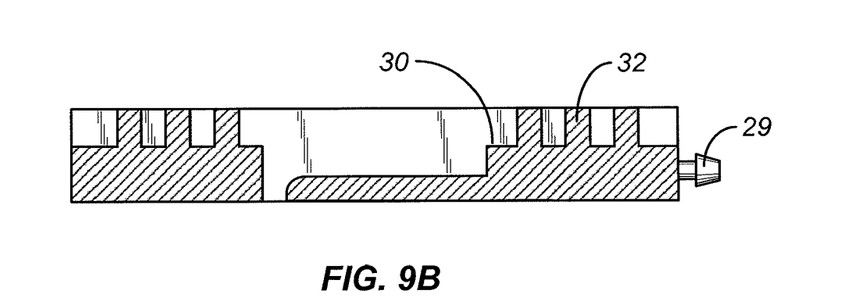
FIG. 9B is a side cross sectional view according to the second embodiment of the invention.
Figure 9C:
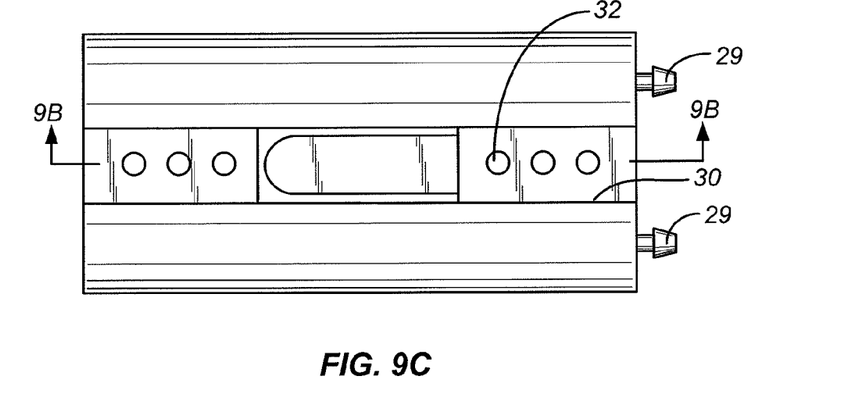
FIG. 9C is a top view according to the second embodiment of the invention.

The scleral buckle of a second embodiment has two configurations: circumferential II1 (FIG. 6A-6C) and radial II2 (FIG. 7). The scleral buckle is assembled with the encircling band E2 to exert indentation effect onto the eyeball, directly on the site where there is retinal break inside the eyeball. There is no lock on the scleral buckle as in the main scleral buckle of Embodiment I. However, there are snap-fit longitudinal grooves 23, 25, 25a along the long axis of the scleral buckle to assemble with the side step 28 of encircling band E2. Moreover, at the base of the groove, there are multiple castellations having a symmetric longitudinal frictional profiles 20, 25 to fit with the complementary symmetric castellations having frictional profiles 27 on the whole length of the encircling band E2 to prevent lateral movement of the scleral buckle from the encircling band when the silicone sleeve is in place. There are lateral snap fit joints 19, 22, 24 (not shown), 26 to assemble with any additional scleral buckle when needed.

The Encircling Band

The length and dimension of the encircling band E2 are the same as in embodiment I E1, but there is no sawtooth profile on each end of the encircling band. Instead, there are multiple castellations with frictional profiles 27 along the whole length of the encircling band E2 to fit with the frictional profiles 20, 25 on the groove 23, 25a of the scleral buckle II1, II2 to prevent lateral movement of the scleral buckle from the encircling band E2.

Resembling embodiment I, the encircling band E2 itself is affixed to the globe by passing through four scleral tunnels 39 made on the eyeball scleral wall (FIGS. 12 and 13). The two ends of the encircling band E2 are then inserted into a short silicone sleeve (not shown) to hold the two ends together and to tighten the encircling band. The two ends of the encircling band E2 are pulled towards each other until both the buckle and encircling band have exerted appropriate indentation effect on the eyeball. Redundant ends of the encircling band E2 after passing through the sleeve are trimmed off.

Moreover, there is a step 28 on either side and along the whole length of the band for snap fit into the groove 23, 25a of the scleral buckle. This is the fastening mechanism for assembly between scleral buckles and encircling band.

Embodiment III

Figure 10:
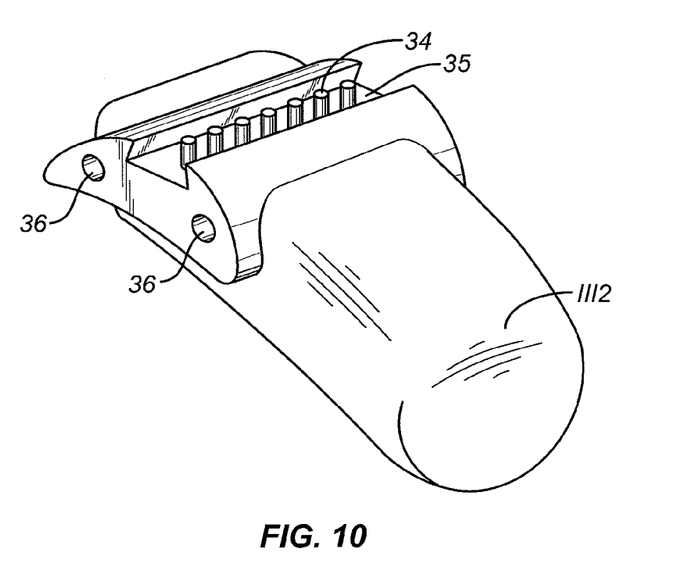
FIG. 10 is a perspective view of a main radial scleral buckle for implantation according to the third embodiment of the present invention.

Embodiment III is similar to embodiment II where there is only one type of scleral buckle (with 2 configurations: circumferential (FIG. 9) and radial (FIG. 10) to assemble with an encircling band E3. The basic principles, materials and rationale for choice of configuration of the scleral buckle are the same as that of embodiments I and II. The difference between embodiment II and embodiment III lies in the method of locking between the scleral buckle and the encircling band. In this embodiment, like embodiment II, a sleeve is used to lock and tighten the two ends of the encircling band together after it has passed through the four scleral tunnels 39. The buckles III1, III2 are assembled with the encircling band E3 to exert an indentation effect onto the eyeball by a different mechanism from embodiment II.

The Scleral Buckle

Figure 11A:
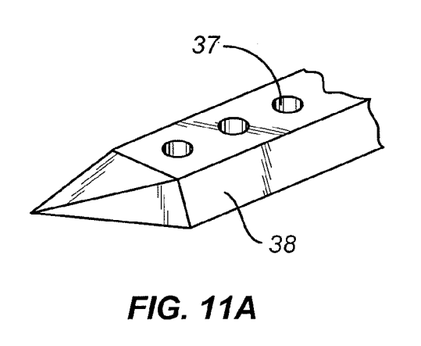
FIG. 11A is a perspective view of an encircling band according to the third embodiment of the present invention showing the exterior of the band.
Figure 11B:
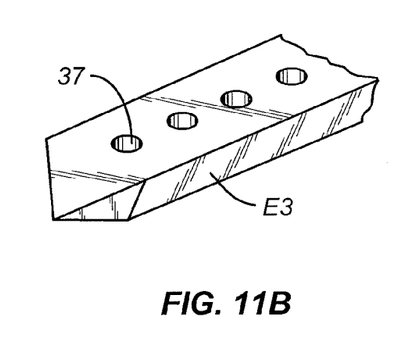
FIG. 11B is a perspective view of an encircling band according to the third embodiment of the present invention showing the interior of the band.

The scleral buckle has two configurations: circumferential III1 and radial III2. The scleral buckles III1, III2 are assembled with the encircling band E3 to exert an indentation effect onto the eyeball directly on the site where there is retinal break inside the eyeball. There is no lock on the scleral buckle. However, there are form fitting spikes 32, 34 (FIGS. 9A-9C and 10) at the base of the groove along the long axis of the scleral buckle to assemble with the row of complementary form fitting holes 37 (FIGS. 11A-11B) along the whole length of encircling band. There are lateral snap fit joints 29, 31, 33 (not shown), 36 to join with any additional scleral buckle when needed.

The Encircling Band

The length and dimension of the encircling band E3 are the same as embodiments I and II. There is a row of complementary form fitting holes 37 along the length of encircling band E3 to fit with the snap fit frictional form fitting spikes 32, 34 at the base of the groove 30, 35 of the scleral buckle III1, III2 to prevent lateral movement of the scleral buckle from the encircling band E3. Resembling embodiment I, the encircling band E3 38 itself is affixed to the globe by passing through four scleral tunnels 39 (FIGS. 12, 13) made on the eyeball scleral wall. The two ends of the encircling band E3 are then inserted into a short silicone sleeve to hold the two ends together and to tighten the encircling band E3. The two ends of the encircling band E3 are pulled towards each other until both the encircling band E3 has exerted appropriate indentation effect on the eyeball. Redundant ends of the encircling band E3 after passing through the sleeve are trimmed off.

Embodiment IV

Figure 14:
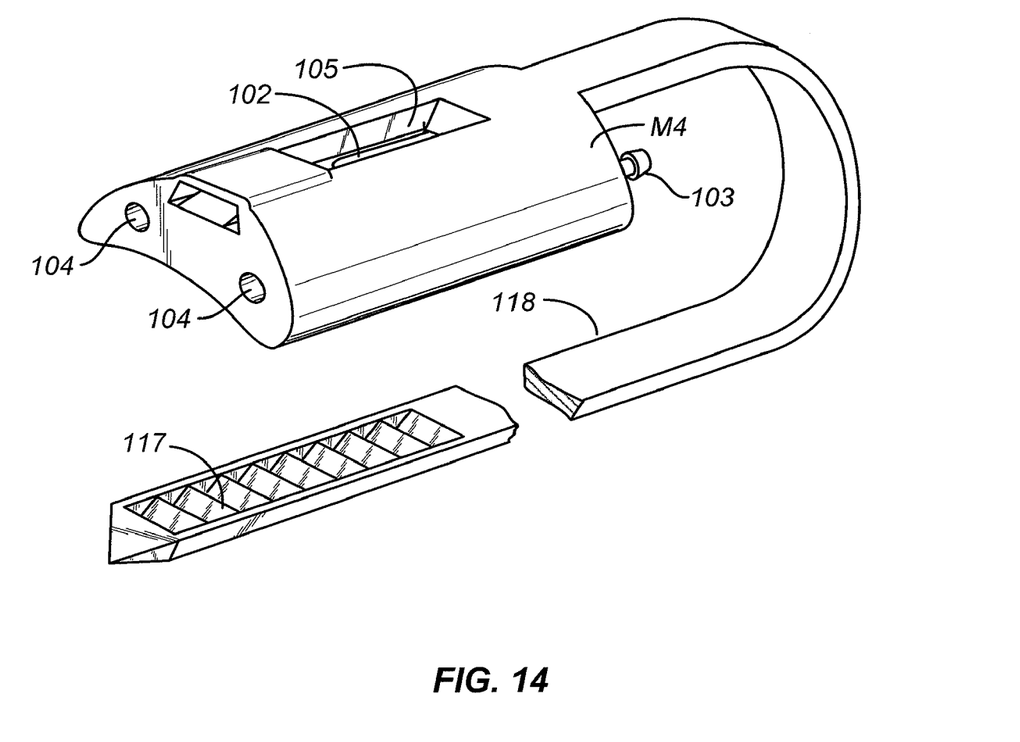
FIG. 14 is a perspective view of a further embodiment of the invention.

In a fourth embodiment, as shown in FIG. 14, the main scleral buckle is combined with the encircling band 118 to form an integrated scleral buckle M4. One end of the encircling band is permanently affixed to and serves as an extension of the main scleral buckle. The other end of the encircling band has asymmetric castellations 117 with a sawtooth profile that serve to lock with the complementary castellations with a sawtooth profile within the snap fit slot 105 of the scleral buckle, resembling embodiment I. There is only one lock in the scleral buckle. The basic principles, material and rationale for choice of configuration of scleral buckle M4 are the same as that of embodiment I. After the free end of the encircling band has passed through the four scleral tunnels, as in FIG. 12, the free end is inserted into the lock of the scleral buckle and the encircling band 118 is tightened by pulling the free end until both the scleral buckle and encircling band have exerted appropriate indentation effect onto the eyeball.

The Scleral Buckle

The main scleral buckle-encircling band combination M4 of the fourth embodiment has two configurations: circumferential IV1 as shown and radial IV2 like FIG. 2, which only varies in the scleral buckle part. The main scleral buckle-encircling band combination M4 is implanted by aligning the buckle portion directly on the site where there is a retinal break inside the eyeball. There is a central tongue structure provided at the base of the groove, and the function is identical to that of embodiment I. Moreover, there are lateral snap fit joints 105 to assemble with any additional supplementary scleral buckle when needed. The supplementary buckle resembles that in embodiment I.

The Encircling Band

The length and dimension of the encircling band 118 are the same as in embodiment I, but there is a sawtooth profile 117 on only one end of the encircling band, which is the free end of the encircling band. Resembling embodiment I, there is a step on either side and along the whole length of the encircling band for snap fit into the groove of any supplemental scleral buckle.

Market Potential

The incidence of rhegmatogenous retinal detachment is 1 per 10,000 population per year, and the incidence could be higher in area with population of high prevalence of myopia such as Hong Kong and Singapore. Scleral buckling surgery is one of two commonly performed operations to treat this type of disease. Scleral buckling (external surgery) is sometimes indicated to combine with pars plana vitrectomy (internal surgery) to treat advance RD. Therefore the application of this invention could be of great help in this field.

This invention has been explained with reference to specific embodiments. Other embodiments may be suggested by this disclosure to those of skill in the art. Therefore it is not intended that this invention be limited, except as indicated by the appended claims.

What is claimed is:

1. A device for treatment of retinal detachment in an eye, the eye having a scleral wall with a plurality of slits around the scleral wall forming tunnels in the scleral wall, the device comprising:
   a main scleral buckle;
   a band;
   the main scleral buckle comprising:
      at least one receptacle; and
      a first structure disposed in the at least one receptacle and configured to capture and secure the band using a first interlocking structure;
   the band comprising:
      at least one end;
      a second structure, corresponding to the first structure of the main scleral buckle, the second structure disposed on the at least one end of the band and configured to be captured by and secured by the first structure of the main scleral buckle using a second interlocking structure that is complementary to the first interlocking structure of the main scleral buckle; and
   the band having an inner surface configured to face the eye; an outer surface configured to face away from the eye, the inner surface and the outer surface defining a first edge that is configured to face in an anterior direction relative to the eye and defining a second edge that is configured to face in a posterior direction relative to the eye, the band having a constant thickness and a constant width along all of the band that does not form the second structure,
   wherein the band has no holes on the inner surface of the band, other than any hole that is part of the second structure,
   wherein the main scleral buckle includes a main scleral buckle inner surface that is curved in an anterior-to-posterior direction and configured to face the eye, and a main scleral buckle outer surface that is curved in an anterior-to-posterior direction and configured to face away from the eye, and wherein both the main scleral buckle inner surface and the main scleral buckle outer surface are wider in the anterior-to-posterior direction than the width of the band, and
   wherein the band is configured to pass through one or more of the tunnels.

2. The device of claim 1 wherein one end of the main scleral buckle is permanently affixed to and connected with the at least one end of the band.

3. The device of claim 1 wherein the main scleral buckle has a circumferential configuration whereby it extends along the band.

4. The device of claim 2 wherein the main scleral buckle has a radial configuration whereby it extends across the band.

5. The device of claim 1 wherein the main scleral buckle has a radial configuration whereby it extends across the band.

6. The device of claim 1 wherein the main scleral buckle has a central groove along its length and the band and the main scleral buckle are configured to engage along the central groove.

7. The device in claim 6, wherein the base of the first structure of the main scleral buckle comprises a plurality of asymmetric castellations in the form of a sawtooth configured to fit complementary sawtooth castellations adjacent the at least one end of the band, in order to tighten the band to prevent movement of the scleral buckle from the band.

8. The device in claim 1, wherein the main scleral buckle has a lateral snap fit joint to enable self-assembly with a supplementary scleral buckle side by side at either end of the buckle to lengthen the whole area of indentation by the main and supplementary buckles.

9. The device of claim 1 further comprising a supplementary scleral buckle, the supplementary scleral buckle being configured to capture the band.

10. The device of claim 1, wherein the first structure of the main scleral buckle comprises two locks along a central groove with a sawtooth profile to lock with the second structure of the band, wherein the second structure comprises a complementary sawtooth profile at the at least one end of the band.

11. The device of claim 1, wherein the band comprises a step on either side and along the length of the band for snap fit into a central groove of the scleral buckle.

12. The device in claim 1, further comprising a plurality of supplementary buckles, wherein the main scleral buckle and the plurality of supplementary scleral buckles are configured to self-assemble side by side at either end of the main scleral buckle anywhere along the encircling band to extend areas of indentation by the main and supplementary scleral buckles.

13. The device in claim 1, further comprising a silicone sleeve, wherein the band comprises two ends that are configured to be locked together directly by the silicone sleeve, to exert substantial indentation by the main scleral buckle and the band onto the eye.

14. The device in claim 1, the first structure comprising:
   a central groove, a plurality of spikes at the base of the central groove along the long axis of the main scleral buckle;
   the second structure comprising:
   a plurality of holes configured to receive the spikes along the band to self-assemble, such that the groove accommodates the band and the spikes prevent lateral movement of the main scleral buckle from the band.

15. The device in claim 14, wherein the band comprises a plurality of form fitting full thickness holes on its inner surface along the length of the band to fit with the complementary spikes.

16. The device in claim 14, further comprising a silicone sleeve, wherein the band comprises two ends and each of the two ends of the band is locked together directly by the silicone sleeve, to exert substantial indentation by the main scleral buckle and the band onto the eye.

17. The device in claim 1, wherein the band comprises two ends, the first structure comprising:
   a central groove, a plurality of symmetric castellations across the central grove at the base of the central groove and arranged along the long axis of the scleral buckle;
   the second structure comprising:
   a plurality of symmetric castellations configured to complement the main scleral buckle such that the groove accommodates the band and the castellations prevent movement of the main scleral buckle from the band when the band is tightened by a sleeve around the two ends of the band.

18. The device in claim 1, wherein the main scleral buckle further comprises
   a tongue configured to fit through a first tunnel and position the main scleral buckle on the eye.

19. The device in claim 18, wherein the tongue is for use where a retinal detachment is located in between rectus muscles and where the main scleral buckle is configured to be implanted between the rectus muscles on top of the retinal detachment, the tongue of the main scleral buckle being configured to be inserted through the tunnel in the quadrant of the retinal detachment to prevent antero-posterior movement of the main scleral buckle.

* * * * *